United States Patent [19]
Hansen et al.

[11] Patent Number: 5,947,934
[45] Date of Patent: Sep. 7, 1999

[54] DOSE DISPLAY FOR AN INJECTION SYRINGE

[75] Inventors: Steffen Hansen, Hillerød; Peter Christian Klitgaard, Smørum, both of Denmark

[73] Assignee: Novo Nordisk A/S, Bagsvaerd, Denmark

[21] Appl. No.: 08/925,702

[22] Filed: Sep. 9, 1997

Related U.S. Application Data

[60] Provisional application No. 60/049,062, Jun. 10, 1997, abandoned.

[30] Foreign Application Priority Data

Sep. 13, 1996 [DK] Denmark .................................. 0991/96

[51] Int. Cl.⁶ ...................................................... A61M 5/00
[52] U.S. Cl. .......................... 604/207; 604/211; 604/232; 604/187
[58] Field of Search .................................. 604/207, 211, 604/232, 155, 187, 224

[56] References Cited

U.S. PATENT DOCUMENTS

| | | | |
|---|---|---|---|
| 4,498,904 | 2/1985 | Turner et al. ............................. | 604/211 |
| 5,697,916 | 12/1997 | Schraga .................................... | 604/201 |

FOREIGN PATENT DOCUMENTS

| | | |
|---|---|---|
| 42 08 677 | 9/1993 | WIPO . |
| WO 94/13343 | 6/1994 | WIPO . |
| WO 96/38190 | 12/1996 | WIPO . |

*Primary Examiner*—Ronald Stright
*Assistant Examiner*—Kent Gring
*Attorney, Agent, or Firm*—Steve T. Zelson, Esq.; Elias J. Lambiris, Esq.

[57] ABSTRACT

The present invention relates to injection syringes comprising a housing accommodating an ampoule containing medicine sufficient for a number of dosed injections. The syringe has a dose setting mechanism by which doses may be set by rotating a dose setting element relative to the housing and the dose set is indicated on a scale. The scale is formed as a clock dial having a first part secured to the housing and a second part which is rotatable relative to the first part and which is coupled to the dose setting element, one of parts carries the scale and the other carries an indicating member indicating a point on the scale. The angular distance between the divisions of the scale corresponds to the minute divisions on an ordinary clock. Holes are provided along the scale which holes can receive a pin forming a stop which cannot be passed by the indicating member.

8 Claims, 1 Drawing Sheet

DOSE DISPLAY FOR AN INJECTION SYRINGE

CROSS-REFERENCE OF RELATED APPLICATIONS

This application claims priority under 35 U.S.C. 119 of U.S. provisional application 60/049,062 filed Jun. 10, 1997 now abandoned and Danish application serial no. 0991/96 filed Sep. 13, 1996, the contents of which are fully incorporated herein by reference.

BACKGROUND OF THE INVENTION

1. Field of the Invention

The invention relates to injection syringes of the kind comprising a housing accommodating an ampoule containing medicine sufficient for a number of dosed injections, the syringe having a dose setting mechanism by which doses can be set from injection to injection by rotating a dose setting element relative to the housing the size of the set dose being indicated on a scale.

2. Description of the Related Art

A problem by the scales is that the perimeter of the syringe sets a limit to the size of the scale and the digits on it. Especially where the syringe is used by people who have impaired sight, as it often may be the case by diabetics, a system allowing use of larger digits on the scale is wanted. Further hints of the size of the set dose may be obtained by studying the distance a injection button is elevated from the syringe but as the elevation pro unit is very small, sometimes of the order 0.15 mm, this will only give an imprecise impression of the size of the dose set.

It is an object of the invention to provide a syringe by which these limitations are overcome.

SUMMARY OF THE INVENTION

This is obtained by a syringe of the kind mentioned in the opening of this specification, which syringe is according to the invention characterised in that the scale is formed as a clock dial having a first part secured to the housing and a second part which is rotatable relative to the first part and which is coupled to the dose setting element, one of parts carries the scale and the other carries an indicating member indicating a point on the scale.

By shaping the dose indicating means as a clock dial this dial may be made arbitrarily large and the size is only limited by the fact that the device must not be too bulky and must be acceptable from a design point of view.

The second part of the dose indicating means may be coupled to the dose setting element through a gear mechanism. This may be necessitated by the fact that the relative rotation of the dose setting means may take place about the longitudinal axis of the syringe whereas the dial is placed so that the relative rotation of the first and the second part takes place around an axis perpendicular to the longitudinal axis of the syringe, however, gear couplings may also be used in syringes wherein the dial and the dose setting means rotate about parallel axes. The geared coupling may also be used to obtain that the relative angular rotation of the first and second part or the dose indicating means may be larger than the relative rotation of the dose setting elements.

As in egg timers a scale carrying divisions and digits may be arranged along the perimeter of the dial with a pointer on the part not carrying the divisions and the digits pointing at a point of the scale indicating the relative rotational position of the dose setting member and the housing and consequently the dose set by this rotation.

According to the invention the syringe may appropriately be of the type using a flexible piston rod to reduce the overall length of the syringe by deflecting the piston rod where it projects from the ampoule. Instead of the ordinary pen shape this type of syringes have a more parallelepiped shape with broad side walls suited as carriers of clock dials.

According to an embodiment of the invention a finger grip may be provided following a diameter on the second part of the dose indicating means, the grip being parallel with the longitudinal axis of the syringe when no dose is set. This grip may be used for setting a dose as rotation of said second part is transmitted to the rotatable dose setting element through the coupling between the second part and the dose setting element. The finger grip will conspicuously indicate whether a dose is set or not as even a small deviation from the position in the axial direction of the syringe is recognisable.

According to a further embodiment of the invention the angular distance between the divisions of the scale is 6° corresponding to the minute divisions of an ordinary clock. This makes it possible to the user to estimate the setting even when he cannot see the digits of the scale. This is due to the fact that the clock dial is so well established by most people that they can read the time on a clock dial without digits, even on a clock dial without divisions. Therefore the position of the indicating member in relation to the scale alone will let the user know the size of a set dose.

From DE 42 08 677 is known a pen shaped injection device having a dose setting mechanism which may be operated via a dose setting element. When not in use the syringe is stored in a box having a dose setting device comprising a large dial shaped scale with divisions and printings. When the syringe is stored in the box a dose may be set by operating the dose setting device on the box and the movements of this device is via a gear mechanism transmitted to the dose setting element of the syringe.

In the device according to the invention the clearly visible dial is carried by the injection device itself so that no setting may be made which is not shown on the dial. Even the device may be so designed that the indication on the dial is successively returned to zero during the injection so that the indication on the dial currently shows the dose which remains to be injected.

The injection syringe may have means by which the setting movement of the dose setting element is limited so that an upper limit is set to the dose which can be set. If by dose setting the dose setting element is moved until it is stopped by the limit a fixed dose is set.

According to an embodiment of the injection syringe according to the invention the limit may be provided by holes provided along the scale which holes each can receive a pin forming a stop which cannot be passed by the indicating member. This makes it possible to put a limit on the dose which may be set as the second part can only be rotated until the indicating member reaches the point on the scale where a pin is inserted in the hole. The pin may be installed by the a user who mostly use the same dose at each injection. When the pin is set in the hole at the division corresponding to the dose in question, the user can set the dose by rotating the second part until the rotation is stopped because the pin reaches a stop which prevent it from passing the indicating member. Alternatively the pin may be mounted by the user's physician to ensure that the user will not inject more than a limited number of units in one injection. Pins used for that purpose may be so designed that a tool is needed to install and remove them. Especially when the device is used by children it is important that an upper limit may be set for the dose which can be injected.

BRIEF DESCRIPTION OF THE FIGS.

In the following the invention will be described in further details with references to the drawing, wherein FIG. 1 shows a pen shaped syringe with a display according to the invention, FIG. 2 shows a new designed short syringe with a display according to the invention FIG. 3 shows an embodiment of a display according to the invention, and FIG. 4 shows another embodiment of a display according to the invention.

DETAILED DESCRIPTION OF THE INVENTION

Figure 1:
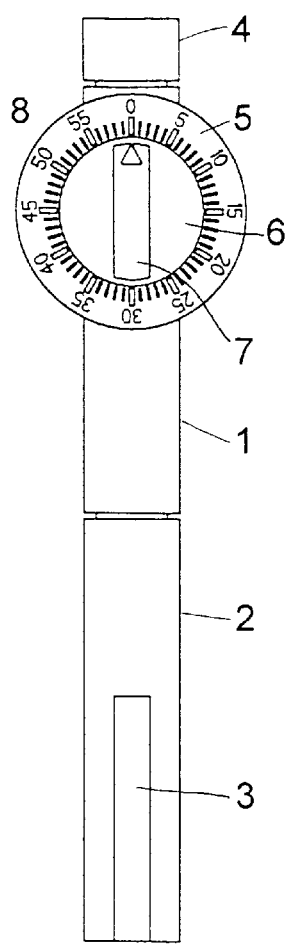

In FIG. 1 is shown a pen shaped syringe comprising, a housing 1 containing a dose setting mechanism, a cap 2 protecting the needle end of the syringe which cap is provided with a clip 3 by which the syringe may be carried in a pocket like a fountain pen, and an injection button 4 which is elevated from the end of the housing 1 concurrently with the setting of a dose and which may be pressed back to abutment with the end of the housing to inject the set dose.

Further the syringe carries a display having the shape of an egg timer dial. The display comprises a scale 5 carrying equidistant marks corresponding to the marks of the minutes on an ordinary watch dial. The scale 5 is fixed to the housing 1. A pointer is established by a circular plate 6 carrying a finger grip 7 having an arrow mark 8. The circular plate 6 and the finger grip 7 form, a dose setting unit by which a dose may be set by gripping the grip 7 and rotating the plate 6 clockwise until the arrow mark points on the mark of the scale indicating the wanted dose. The plate 6 with the finger grip 7 is mounted on a not shown shaft which is journaled in the housing and through which combined with a gear mechanism the rotation of the dose setting unit is transmitted to a conventional dose setting mechanism in the housing 1. The plate 6 may be omitted so that the dose setting unit comprises only the finger grip 7.

Figure 2:
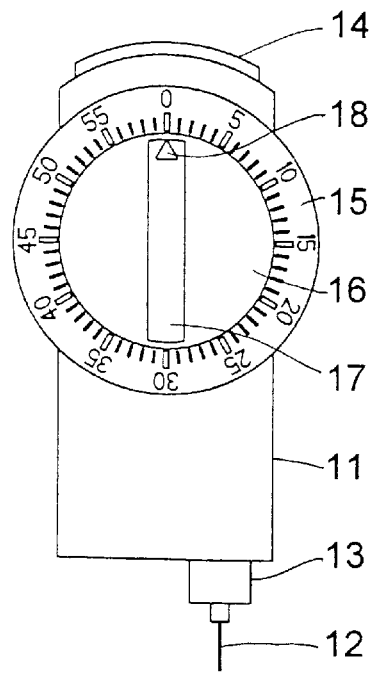

The embodiment shown in FIG. 2 represents another type of syringes which due to the use of a flexible piston rod are made shorter than the pen type. The pen comprises a housing 11 containing a dose mechanism and accommodating a cartridge with a medicine to be apportioned. An injection needle 12 is mounted in a needle hub 13 which may be screwed onto the syringe. The end of the syringe carrying the needle may be covered by a not shown protection cap. The syringe has an injection button 14 which is elevated from the end of the housing 11 concurrently with the setting of a dose and which may be pressed back to abutment with the end of the housing to inject the set dose. Also in this embodiment a scale 15 is fixed on the housing and the dose is set by rotating clockwise a dose setting unit comprising a circular plate 16 carrying a finger grip 17 with an arrow mark 18 until the arrow mark point at the mark corresponding to the wanted dose. This rotation is transmitted through a not shown shaft carrying the dose setting unit and transmitting rotation of this unit to a dose setting mechanism in the housing. The button 14 is pressed home to abutment with the housing to inject the set dose and concomitantly with the injection the dose setting unit is rotated back so that the arrow mark points at the zero mark of the scale to indicate that the full dose is delivered.

Advantage is taken of the fact that watching a clock dial is so well promoted that most people will be able to estimate the minute number by just watching the position of a mark along the periphery of a circle. By making the divisions which indicates the set number of units of the medicine to be injected correspond to the minute divisions of a clock dial, the user will be able to estimate the size of a set dose with high precision even when the dose size is not indicated by a number at each division mark. When e.g. only every fifth division mark is provided with an dose indicating number, the digit of this number may be made very large an easy readable.

Figure 3:
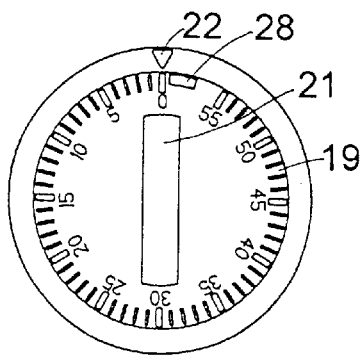

To take the full advantage of this fact it is preferred that the finger grip is rotated clockwise when a dose is set. In FIG. 3 where a scale 19 is carried by a circular plate 20 of a dose setting unit which may be rotated by a finger grip 21 and the arrow mark 22 is fixed in relation to the housing this clockwise rotation is obtained by positioning the scale marks and the numbers of the scale in an anticlockwise fashion. This way a clockwise rotation of the dose setting unit will bring increasing numbers abreast of the arrow mark.

In FIG. 3 the scale has a wide mark 28 which may be pointed at by the arrow when the finger grip is rotated anticlockwise. A stop is established so that the scale only be rotated further anticlockwise until the arrow points at the mark 28. By this anticlockwise rotation a fixed small dose is set, e.g. corresponding to delivery of 10µl of the medicine. This small dose is set before the dose to be injected is set and is pressed out by pressing the injection button. Thereby air in the ampoule or and the needle is pressed out through the needle an visual inspection of the jet at the end of the needle can reveal if the air is expelled. The setting by anticlockwise rotation of the finger grip and subsequent pressing the injection button is repeated until a jet of liquid is seen at the end of the needle. The provision of the possibility of setting a small dose by anticlockwise rotation of the finger grip may be seen as a feature easing the air shot procedure which should else be performed by repetitively setting of small doses in the conventional way by clockwise turning of the finger grip.

Figure 4:
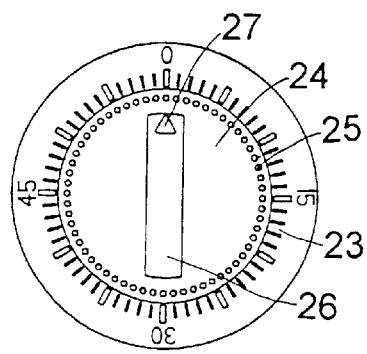

In FIG. 4 is shown another display with a scale 23 which is fixed in relation to the housing. The dial carrying the scale 23 have a central part 24 which is also fixed relative to the housing and which at every mark of the scale indicating a unit of the medicine to be injected has a hole 25 into which a not shown pin may be inserted. The dose setting unit only consist of a finger grip 26 with an arrow mark 27 which unit is carried by a not shown shaft transmitting the rotation of the unit to a dose setting mechanism. Behind the dial carrying the scale said shaft has a pointer parallel with the finger grip and pointing from the shaft in the direction of the arrow mark. When a pin is mounted in one of the holes in the dial the pointer will abut this pin when the dose setting unit is rotated and will stop for further rotation in the dose setting direction but will allow the unit to rotate back when a set dose is injected. This way it may be ensured that a set maximum dose is not exceeded. It is further shown that the dose mark does not have to be numbered at each 5 units but e.g. only at each 15 units. In fact most designs known from egg timers and similar clocks may be used without deviating from the scope of the invention.

We claim:

1. An injection syringe comprising:
   a housing accommodating an ampoule containing medicine sufficient for a number of dosed injections, a dose setting mechanism including a dose setting element which is rotatable relative to the housing and by which doses may be set by rotating a dose setting element an injection button which is moved relative to the housing in response to rotating the dose setting element and which, when pressed, administers the set dose, and a scale for indicating the set dose, having the general configuration of an egg timer dial, wherein the scale bears scale markings corresponding to a clock dial, wherein said scale has a first part fixedly secured to the housing and a second part which is rotatable relative to the first part, wherein the second part includes a grip, and is coupled to the dose setting element for rotating the dose setting element in order to set a dose, and wherein one of the parts carries the scale markings and the other g carries an indicating member indicating a point on the scale markings.

2. An injection syringe according to claim 1, wherein the second part is coupled to the dose setting element through a gear mechanism.

3. An injection syringe according to claim 1, wherein the syringe is of the type using a flexible piston rod.

4. An injection syringe according to claim 1, wherein the syringe has a longitudinal axis, wherein the second part has an axis of rotation, and wherein the grip extends perpendicular to the axis of rotation of the second part and is parallel with the axis of the syringe when no dose is set.

5. An injection syringe according to claim 1, wherein the angular distance between the scale markings of the scale is 6° corresponding to the minute divisions on an ordinary clock.

6. An injection syringe according to claim 1, further comprising means by which the setting movement of the dose setting element is limited so that an upper limit is set to the dose which can be set.

7. An injection syringe according to claim 6, wherein holes are provided along the scale which holes can receive a pin forming a stop which cannot be passed by the indicating member.

8. An injection syringe according to claim 1, wherein said grip is coupled to the dose setting element such that clockwise rotation of the grip sets a dose.

* * * * *

UNITED STATES PATENT AND TRADEMARK OFFICE
CERTIFICATE OF CORRECTION

PATENT NO. : 5,947,934
DATED : September 7, 1999
INVENTOR(S) : Hansen et al.

It is certified that error appears in the above-identified patent and that said Letters Patent is hereby corrected as shown below:

Column 5,
Line 16, please delete "g", and insert -- part --.

Signed and Sealed this

Eleventh Day of December, 2001

Attest:

NICHOLAS P. GODICI
Attesting Officer  Acting Director of the United States Patent and Trademark Office